(12) United States Patent
Krill et al.

(10) Patent No.: US 6,350,897 B2
(45) Date of Patent: Feb. 26, 2002

(54) PROCESS FOR PREPARING TRIMETHYLHYDROQUINONE DIACETATE AND TRIMETHYLHYDROQUINONE

(75) Inventors: Steffen Krill, Speyer; Klaus Huthmacher, Gelnhausen, both of (DE)

(73) Assignee: Degussa AG, Hanau (DE)

( * ) Notice: Subject to any disclaimer, the term of this patent is extended or adjusted under 35 U.S.C. 154(b) by 0 days.

(21) Appl. No.: 09/825,361

(22) Filed: Apr. 4, 2001

(30) Foreign Application Priority Data

Apr. 7, 2000 (DE) .......................................... 100 17 494

(51) Int. Cl.⁷ .............................................. C07C 69/00
(52) U.S. Cl. ............................ 560/144; 560/1; 560/109
(58) Field of Search ............................ 560/144, 1, 109

(56) References Cited

U.S. PATENT DOCUMENTS 4,247,720 A * 1/1981 Baudouin et al.

FOREIGN PATENT DOCUMENTS

EP 0850912 * 2/1999

OTHER PUBLICATIONS

Bull. Korean Chem. Soc. 1991, 12 p. 253.*

Journal Mol. Cat. 172, 427–435 (1997).*

* cited by examiner

*Primary Examiner*—Paul J. Killos
(74) *Attorney, Agent, or Firm*—Smith, Gambrell & Russell LLP

(57) ABSTRACT

A process for preparing trimethylhydroquinone diacetate, with subsequent hydrolysis to give trimethylhydroquinone, the process including reacting 2,2,6-trimethylcyclohexane-1,4-dione under oxidative conditions, in the presence of a sulfonating agent and a strong acid, and in the presence of an acylating agent.

14 Claims, No Drawings

PROCESS FOR PREPARING TRIMETHYLHYDROQUINONE DIACETATE AND TRIMETHYLHYDROQUINONE

BACKGROUND OF THE INVENTION

1. Field of the Invention

The invention relates to a process for preparing 2,3,5-trimethylhydroquinone diesters (TMHQ-DA) by the oxidative aromatization of 2,6,6-trimethylcyclohexane-1,4-dione (dihydro-ketoisophorone=DH-KIP), by reaction with a sulfonating agent in the presence of an acylating agent, and in the presence of an acid catalyst which may be present in the reaction medium either in dissolved form or else as a heterogeneous solid catalyst. The trimethyl-hydroquinone diesters obtained may be converted directly to vitamin E acetate by reaction with phytol derivatives, in particular isophytol (IP), or may instead be first hydrolyzed in the presence of suitable catalysts to give trimethylhydroquinone (TMHQ), which can then be converted into vitamin E by condensation with isophytol derivatives followed by acylation to give vitamin E acetate.

DE-OS 2 149 159 discloses the rearrangement of KIP in the presence of acetanhydride, in a rearrangement reaction catalyzed by proton or Lewis acids, to give trimethylhydroquinone diacetate, which is then saponified to give TMHQ. In order to achieve complete conversion, large excesses of acid have to be used. The resulting isolation yields (maximum 66%, with respect to the ketoisophorone used) are unsatisfactory because costly recrystallization procedures are required due to the presence of secondary products.

DE-OS 196 27 977 discloses the rearrangement of KIP in the presence of stoichiometric amounts of acetanhydride and catalytic amounts of various acids (trifluoromethanesulfonic acid, chlorosulfonic acid, and oleum, in various concentrations).

Other processes which describe basically the same procedure, that is, the reaction of ketoisophorone with acetanhydride or acetic acid in the presence of a proton acid to give trimethylhydroquinone diacetate, are described in EP 0 850 912 and EP 0 916 642 A1 and JP OS 11-49712. (Suyama et al., 23.2.99; rearrangement of KIP in the gas phase in the presence of a heterogeneous acidic solid catalyst).

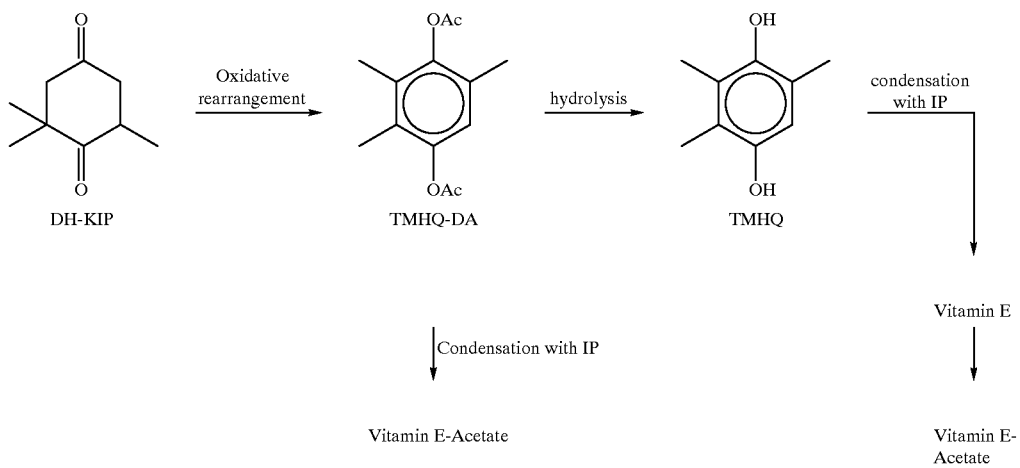

DH-KIP → (Oxidative rearrangement) → TMHQ-DA → (hydrolysis) → TMHQ → (condensation with IP) → Vitamin E-Acetate TMHQ-DA → (Condensation with IP) → Vitamin E-Acetate TMHQ → Vitamin E → Vitamin E-Acetate 2,3,5-trimethylhydroquinone and 2,3,5-trimethylhydroquinone diesters are very important intermediates in the synthesis of vitamin E and other chromane compounds which are pharmaceutically active substances and which are used, inter alia, as antioxidants. Vitamin E-acetate, in turn, is used in the form of special formulations as an animal feedstuffs additive in addition to applications in the human sector.

2. Description of the Related Art

To produce 2,3,5-trimethylhydroquinone diesters, 4-oxoisophorone (KIP) is normally used as the initial reactant, which can be rearranged in the presence of strong acid catalysts and an acylating agent such as carboxylic anhydrides or acyl halides. The rearrangement of ketoisophorone (KIP) is described in U.S. Pat. No. 4,247,720, which describes rearrangement in the gas phase under hydrogenating conditions. With maximum conversions of 30%, a selectivity to give a TMHQ yield of only 50% is achieved.

Bull. Korean Chem. Soc. 1991, 12, pages 253 et seq., discloses the rearrangement of KIP in a 5% strength solution in acetanhydride, with the addition of 5 equivalents of concentrated sulfuric acid. The TMHQ-DA yields achieved are only 30%.

A common feature of all these processes is that the trimethylhydroquinone ester, and the trimethylhydroquinone obtainable therefrom by hydrolysis, are prepared starting from a non-aromatic starting compound, that is 2,6,6-trimethylcyclohex-2-ene-1,4-dione. In this reaction, the initial reactant (KIP) already has the same oxidation state as the product, TMHQ-DA, which means that the reaction can be explained by a simple Wagner-Meerwein rearrangement. The diagram given below reproduces the reaction normally used to prepare TMHQ-DA:

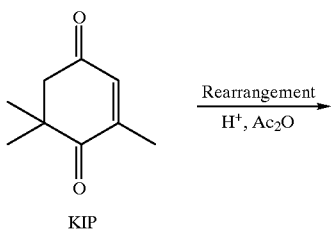

KIP → (Rearrangement, $H^+$, $Ac_2O$)

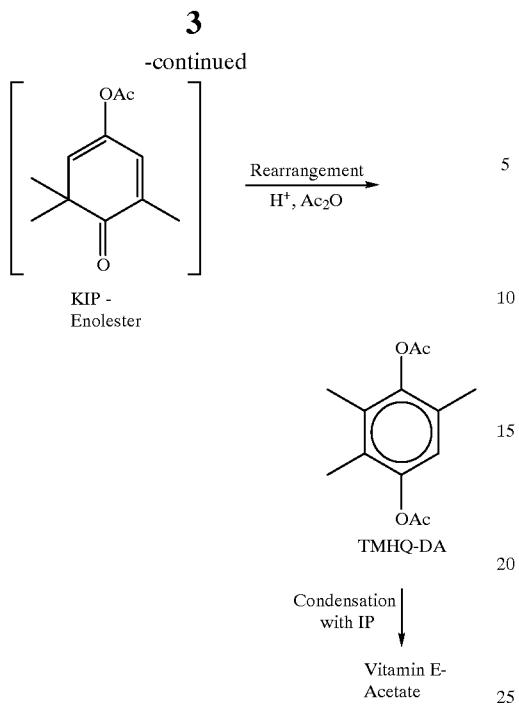

KIP - Enolester

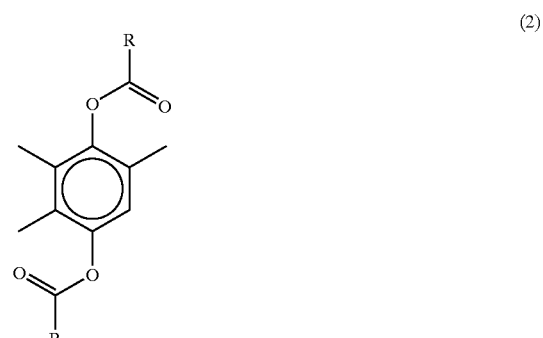

TMHQ-DA

Condensation with IP

Vitamin E-Acetate

The KIP enolester can be detected when following the course of the reaction using gas chromatography, from which it is assumed that the enolester is the intermediate product of the reaction.

However, the ketoisophorone used for the synthesis is relatively expensive as a starting material. It is obtained using known processes by the oxygen oxidation of β-isophorone. The mixture obtained is then worked up by distillation.

To prepare TMHQ-DA, 2,2,6-trimethylcyclohexane-1,4-dione (DH-KIP=dihydro-KIP) is especially interesting, this being obtainable by oxidation, starting from β-isophorone, via β-isophorone epoxide and 4-hydroxyisophorone. The preparation of the aliphatic 1,4-diketone (DH-KIP) or its precursor 4-hydroxyisophorone (HIP) is described, for example, in the following references:

Journal Mol. Cat. 172, 427–435, (1997) discloses the epoxidation of β-isophorone with tert-butyl-hydroperoxide as oxidizing agent, in the presence of a heterogeneous catalyst ($SiO_2$-$TiO_2$ solid catalyst), giving β-isophorone epoxide (β-IPO) and 4-hydroxy-isophorone (HIP).

Tetrahedron Lett., Suppl. 8, Part I, 1–7, discloses the oxidation of β-isophorone to β-IP epoxide by oxidation with meta-chlorobenzoic acid, followed by isomerization in basic medium, to give HIP, which is rearranged to give DH-KIP (yield: 78%), in the presence of an apolar solvent and in the presence of catalytic amounts of p-toluenesulfonic acid.

Helv. Chim. Acta 39, 2041 (1956) discloses the oxidation of β-IP with peracetic acid as oxidizing agent, followed by treatment of the reaction product with NaOH, and the formation of HIP in 57% yield.

DP 38 06 835 discloses the oxidation of β-IP by reaction with aqueous hydrogen peroxide in the presence of formic acid to give HIP, with simultaneous back-isomerization of β-IP to alpha-isophorone.

The object of the present invention is to find alternative aliphatic initial reactants for TMHQ-DA synthesis which are readily obtainable, and to find a process for the efficient reaction of this alternative initial reactant to give TMHQ diesters.

SUMMARY OF THE INVENTION

The present invention relates to the use of dihydro-ketoisophorone (DH-KIP) as an alternative initial reactant for the synthesis of TMHQ-DA. The invention relates also to an economically viable process for this reaction. It is intended that both the requisite oxidation reaction as well as the rearrangement reaction involving aromatization be performed in a single process step.

DETAILED DESCRIPTION OF THE INVENTION

The present invention thus relates to a process for preparing trimethylhydroquinone diesters of the general formula (2)

wherein R represents an optionally substituted aliphatic, alicyclic or aromatic hydrocarbon group, and to a process for preparing 2,3,5-trimethyl-hydroquinone of the general formula (3)

by reacting 2,2,6-trimethyl-cyclohexane-1,4-dione of the general formula (1)

(1)

with an acylating agent, the reaction being performed under oxidative conditions, with a sulfonating agent, and in the presence of a proton acid and/or a Lewis acid, at a temperature between −50° C. and 200° C., wherein the ratio between acylating agent and 2,2,6-trimethyl-cyclohexane-1,4-dione is at least 1.

The reaction of DH-KIP as an initial reactant in the preparation of TMHQ-DA has not heretofore been used because the saturated 1,4-diketone does not have the appropriate oxidation state to ensure successful reaction by a simple rearrangement to TMHQ-DA.

By means of the process according to the invention, however, it is now possible to use DH-KIP as an initial reactant for the synthesis of trimethylhydroquinone diesters and trimethylhydroquinone. The reaction according to the invention is shown in the following diagram:

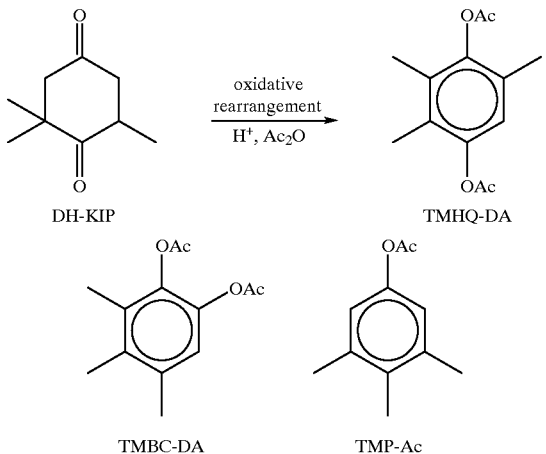

As shown in the reaction scheme given above, the reaction also leads to trimethyl-pyrocatechol diacetate (TMBC-DA) and to 3,4,5-trimethylphenol acetate (TMP-Ac), in addition to trimethylhydroquinone diacetate, depending on the reaction conditions.

The invention provides a new process for preparing 2,3,5-trimethylhydroquinone diesters, and trimethylhydroquinone, by the rearrangement of 2,2,6-trimethyl-cyclohexane-1,4-dione (dihydroketoisophorone= DH-KIP) by reaction with an acylating agent in the presence of an acid proton-containing catalyst with a $pK_a$ value or 3 or less, and/or a Lewis acid, under oxidizing conditions. In a straightforward example of the process according to the invention, the catalyst acid used for rearrangement is also the oxidizing agent, in particular sulfuric acid or oleum. According to a further variant, however, the oxidative rearrangement of DH-KIP in the presence of an acylating agent may also be catalyzed by a non-oxidizing Brönsted or Lewis acid, wherein in this case a sulfonating agent such as, for example, sulfuric acid/oleum, must also be present.

The reaction takes place at temperatures from −50 to 200° C., wherein the ratio of acylating agent to DH-KIP is at least 1:1. The reaction is preferably performed in the temperature interval from −20 to 120° C. At higher temperatures, the selectivity for TMHQ diester formation decreases in favor of the formation of secondary products such as trimethylphenol acetate and trimethylpyrocatechol diesters. At lower temperatures, high product selectivity can be achieved, but the rate of reaction decreases.

The TMHQ diester obtained at the end of the reaction can be reacted directly with isophytol to give vitamin E acetate, after isolation and under suitable conditions. As an alternative to this procedure, the diester obtained as an intermediate product is hydrolyzed to give trimethyl hydroquinone, with the addition of water to the reaction mixture.

The acylating agent used in the process is preferably a carboxylic anhydride, carboxylic acid halide, enolester, ketene or some other acylating agent known in the art. Carboxylic anhydrides with the general formula (4) given below are particularly preferred:

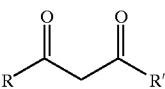

(4)

wherein R and R' are identical or different substituents and represent an optionally substituted aliphatic, alicyclic or aromatic group having from 1–10 carbon atoms, which may optionally be halogenated.

In the context of the invention, acetanhydride is particularly preferred for use as an acylating agent. Another advantage of using acetanhydride is the production of acetic acid during the reaction, this being a suitable phase-promoter for the subsequent hydrolysis reaction with water to give TMHQ. Other suitable acid anhydrides are the anhydrides of propionic acid, butyric acid, isobutyric acid, cyclohexanoic acid, benzoic acid, or the anhydrides of monohalogenated or polyhalogenated carboxylic acids. Chloroacetic acid and trifluoroacetic acid, for example, may be mentioned. Cyclic anhydrides such as, for example, maleic anhydride or succinic anhydride are also suitable as acylating agents in the reaction. Also, there are no restrictions on the use of carboxylic acid halides, wherein good results are obtained in particular with the chlorides corresponding to the carboxylic acids listed above. The use of acetyl chloride as an acylating agent is particularly preferred.

The acylating agent should preferably be present in a molar ratio of at least 1:1 with respect to the DH-KIP used, preferably in a molar ratio of 1:1 to 1:10. The use of higher concentrations of acylating agent does not interfere with the reaction, but no further improvement in reaction is produced by these high dilutions. In this case, the excess acylating agent is used as a solvent which can be separated from the product and recycled in a simple manner by distillation after production of the TMHQ diester required as the target product.

When using carboxylic acid halides, the same data with regard to molar ratios apply as were mentioned in the case of using anhydrides. The use of acetyl chloride, propionyl chloride and butyryl chloride may be mentioned, for example, for use as carboxylic acid chlorides. As an example of the use of enolesters, isopropenyl acetate and structurally related compounds of the following general formula (5) may be mentioned here:

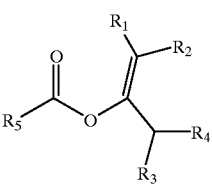

(5)

wherein $R_1$, to $R_4$ represent H atoms or hydrocarbon groups having 1–10 carbon atoms, or a 5 or 6-membered alicyclic hydrocarbon, and $R_5$ represents an aliphatic, alicyclic or aromatic hydrocarbon group, optionally substituted, having 1 to 10 carbon atoms.

In the process according to the invention, rearrangement of the 1,4-dione has to be performed under oxidative conditions. In the simplest case, the catalyst acid used also takes on the function of the oxidizing agent. According to the invention, oxidizing acids with a $pK_a$ value of 3 or less are suitable for rearranging DH-KIP to give TMHQ diesters, in particular sulfuric acid and oleum, with a variety of $SO_3$ concentrations.

Particularly suitable for the process according to the invention are sulfonating reagents, such as sulfuric acid or oleum, with a variety of $SO_3$ concentrations. Also suitable are mixtures of sulfuric acid with boric acid and oleum with boric acid. When using these reagents, the reaction takes place with sulfonation occurring in situ, wherein $SO_2$ is given off in a subsequent step.

When using sulfuric acid, oleum, and similar sulfonating reagents, additional non-oxidizing acid catalysts may also be added in order to accelerate the reaction. In principle, both proton acids and Lewis acids are suitable. Examples of Brönsted acids which can be used are mineral or organic acids with a $pk_a$ value of 3 or less, including aliphatic or aromatic sulfonic acids such as para-toluenesulfonic acid, benzenesulfonic acid, methanesulfonic acid, ethanesulfonic acid, hydrohalic acids (HX; X=F, Cl, Br, I), phosphoric acid and aliphatic and aromatic phosphonic acids, haloacetic acids ($XCH_2CO_2H$; X=F, Cl, Br) or the corresponding polyhalogenated derivatives such as trichloroacetic acid or trifluoroacetic acid, nitroterephthalic acid or corresponding aryl carboxylic acids which are activated by electron-attracting substituents.

Particularly preferred proton acids which can be used in addition to the sulfonating reagents are catalyst systems which contain, on the one hand, boric acid, and, on the other hand, carboxylic acids or other chelating ligands. The action of these catalyst systems is based on the catalyst species being formed in situ from the boron-containing compound, on the one hand, and the carboxylic acid used, on the other hand, the $pK_a$ value of this species being lower than the $pK_a$ value of boric acid. Particularly suitable in this regard are mixtures of boric acid or appropriate boric acid derivatives and oxalic acid, wherein the ratio of the catalyst components is between 1:10 and 10:1.

In another variant, the process is performed in the presence of a proton acid having a Hammett constant $H_0<-11.9$. Acids covered by this classification include the so-called superacids such as perchloric acid, halosulfonic acids (chlorosulfonic acid, fluorosulfonic acid, etc), and perhaloalkanesulfonic acids such as, for example, perfluoroalkanesulfonic acids of the general formula (6):

$$C_nF_{2n+1}SO_3H \quad (6)$$

wherein n may be from 1–8.

Solid catalysts, which have advantages over homogeneously dissolved proton acids during the working up procedure due to the ease of separation after the end of reaction, may also be used as acids. These solid catalysts include strongly acidic and superacidic ion exchangers, various acidic mixed oxides, zeolites (Y, X, A, or βtype), and heteropolyacids (heteropolyacids which are composed, inter alia, from the elements P, Mo, V, W and Si). Acidic ion exchangers are, in particular, common ion exchangers in which the acidity is produced by $-SO_3H$ groups on a suitable support (for example Amberlyst catalysts, or Deloxane; Degussa AG). The sulfonic acid groups may be bonded, inter alia, covalently to an organic or inorganic supportmaterial. Superacidic solid acids may also be used (for example those of the Nafion type, such as Nafion NR50 from Aldrich or Nafion H from Dupont), wherein the acidity here is produced by perfluoroalkanesulfonic acid groups which are bonded to various support materials. Insoluble sulfates which are acidic under the reaction conditions, e.g. $CaSO_4$, $Fe_2(SO_4)_3$, $CuSO_4$, $NiSO_4$, $(Al)_2(SO_4)_3$, $MnSO_4$, $BaSO_4$, $CoSO_4$, $ZnSO_4$, $(NH_4)SO_4$, may also be used. Examples of acidic mixed oxides which may be mentioned include $SiO_2$—$Al_2O_3$, $SiO_2$—$TiO_2$, $TiO_2$—$ZrO_2$, $SiO_2$—$ZrO_2$, and related compounds. Also suitable are zeolites, including ZSM-5, mordenite, and acidic aluminium phosphate systems. Various Lewis acids and proton acids, which have already been mentioned above, fixed to a support material, are also suitable as solid catalysts. Examples which may be mentioned here are $SbF_5$, $TaF_5$, $BF_3$, $AlX_3$ (X=Cl, Br, F), $SbF_5$—HF, $SbF_5$—$FSO_3H$, $SbF_5$—$CF_3SO_3H$, $SO_4^{2-}$, and compounds with equivalent acidity. The previously specified compounds also include superacids which have a Hammett constant $H_0<-11.9$.

The solid catalyst may be used as a slurry or else, in an appropriate form, introduced into a fixed bed reactor.

The process may be performed in the presence of an organic solvent which behaves in an inert fashion under the reaction conditions. The concentration of reactants in the solvent has only a minor effect on the product mixture for the reaction, and has an effect only on the ratio between trimethylhydroquinone diesters and the corresponding pyrocatechol diesters. The reaction is preferably performed without any solvent, so that solvent distillation and separation from the product are not required.

If the rearrangement takes place in the presence of organic solvents, in particular aliphatic and cyclic esters, for example ethyl acetate, propyl acetate, butyl acetate, isobutyl acetate, gamma-butyrolactone, ethylene carbonate, their derivatives and homologues; aliphatic, alicyclic and aromatic hydrocarbons, for example pentane, hexane, heptane, octane and other homologues, benzene, toluene or xylene are used. Ketones are also suitable as solvents in the context of the invention, such as, for example, acetone, methyl-ethyl ketone, diethyl ketone or isophorone. Furthermore, aliphatic, aromatic or mixed ethers such as diethyl ether, methyl-tert-butyl ether may be used.

In one embodiment of the process, the trimethylhydroquinone diester being produced is crystallized directly from the carboxylic acid being produced during reaction, without needing to add another solvent. However, it is also possible to achieve isolation of the product (and thus the removal of secondary products such as trimethylphenol esters and pyrocatechol diesters) by adding a suitable solvent after distilling off the free carboxylic acid being produced. In another embodiment, the reaction is performed in one of the solvents mentioned, and product isolation is performed by crystallization directly from the solvent for the reaction. The purity of the TMHQ-DA isolated in this way corresponds to the product quality which is required for use as an initial reactant in vitamin E acetate synthesis.

In another embodiment, the TMHQ diacetate being produced is saponified without isolation, by adding water to the crude mixture from the reaction. The presence of the carboxylic acid produced during TMHQ-DA formation, in this case acetic acid, is advantageous because it acts as a phase promoter and ensures efficient hydrolysis of the diester. The same catalyst may be used as a saponification catalyst as was used for the oxidative rearrangement of DH-KIP. Free trimethyl-hydroquinone TMHQ is isolated in a manner known per se by crystallization from an appropriate medium. TMHQ may also be synthesized after the intermediate isolation of TMHQ-DA, wherein hydrolysis is then performed in the presence of a basic or acidic catalyst, optionally in the presence of a phase-promoting compound such as, for example, acetic acid, n-butanol or n-butyl acetate. It is also possible to convert TMHQ-DA into TMHQ by hydrolysis under pressure in the presence of a catalyst.

The following examples are provided for purposes of illustration, and are not intended to limit the scope of the invention in any way.

EXAMPLES

Example 1
Reaction of DH-KIP With Acetanhydride/acetic Acid in the Presence of Sulfuric Acid 0.6 gram (g(10 mmol)) of acetic acid are added to 1.54 g of dihydro-ketoisophorone (DH-KIP), and a suspension is formed by stirring. To this suspension is added, with stirring at room temperature, 10.21 g of acetanhydride (100 mmol). To this colourless solution is added, using an injection pump and over the course of 10 minutes, concentrated 96% sulfuric acid (721 ml; 13 mmol; 130 mol. % w.r.t. to DH-KIP). The continuous evolution of $SO_2$ is observed during the time of addition. After completion of sulfuric acid addition, the mixture is heated for 3 hours at 100° C., then cooled to 20° C., wherein crystals separate out. For complete crystallization, 5 ml of water are added to the suspension, and crystallization takes place at 20° C. The crystals are washed with a little cold acetic acid, and colourless crystals are obtained, which are identified as pure trimethylhydroquinone diacetate, after drying under vacuum at 55° C. The conversion of DH-KIP is quantitative.

Yield: 1.95 g (82.5% of theoretical)
Purity: 99.3% (HPLC)

Example 2
Reaction of DH-KIP With Acetanhydride in the Presence of Sulfuric Acid 1.54 g (10 mmol) of DH-KIP are placed in a three-necked bulb and concentrated 96% sulfuric acid (13 mmol) and 5.1 g of acetanhydride (50 mmol) are added one after the other, with cooling by an external water bath so that the temperature does not exceed 30° C. Then the mixture is stirred for 3 hours at 30° C. After quantitative GC analysis of the reaction mixture obtained in this way, the following results are obtained:

| | |
|---|---|
| Conversion of DH-KIP: | 99.14% |
| Yield of TMHQ-DA: | 93.6% (i.e. selectivity: 94.4%) |
| Yield of TMBC-DA: | 4.6% (i.e. selectivity: 4.6%) |

Example 3
Reaction of DH-KIP With Acetanhydride in the Presence of Sulfuric Acid at 50° C.

1.54 g (10 mmol) of DH-KIP and concentrated 96% sulfuric acid (13 mmol) are initially introduced into a three-necked bulb at 50° C., and 5.1 g of acetanhydride (50 mmol) are added thereto, wherein the temperature is held at 50° C. by regulating the rate of addition. Then the mixture is stirred for 3 hours at 50° C. Following quantitative GC analysis of the reaction mixture obtained in this way, the following results are obtained;

| | |
|---|---|
| Conversion of DH-KIP: | 100% |
| Yield of TMHQ-DA: | 91.2% (i.e. selectivity: 91.2%) |
| Yield of TMBC-DA: | 5.2% (i.e. selectivity: 5.2%) |

Example 4
Reaction of DH-KIP to Give TMHQ-DA With Acetanhydride/acetic Acid, in the Presence of Sulfuric Acid, and Then Hydrolysis to Give TMHQ 15.4 g of DH-KIP (100 mmol) were dissolved in 20 g (0.33 mol) of acetic acid at room temperature, and the solution was cooled to 5° C. with stirring. Then, over the course of 10 minutes, 13.3 g (130 mmol) of concentrated 96% sulfuric acid were added. The clear solution was then heated to 50° C. and 102.1 g of acetanhydride (1 mol) were added via an injection pump over the course of 0.5 hours. Finally, the mixture was stirred for 2 hours at 50° C. Quantification of the reaction solution using GC provided the following results.

| | |
|---|---|
| Conversion of DH-KIP: | 100% |
| Yield of TMHQ-DA: | 93.2% (i.e. selectivity: 93.2%) |
| Yield of TMBC-DA: | 4.3% (i.e. selectivity: 4.3%) |

The reaction solution was hydrolyzed with 100 ml of water and heated for 3 hours under reflux to complete the hydrolysis reaction. Then the mixture was concentrated on a rotary evaporator and crystallized with the addition of water. Colourless crystals were obtained at 20° C., and these contained <1% TMBC according to GC.

Conversion of TMHQ-DA: 99.2%
Yield of TMHQ: 13.5 g; 88.5% of theoretical with respect to DH-KIP
GC concentration: 99.3%

Further variations and modifications will be apparent to those skilled in the art from the foregoing, and are intended to be encompassed by the claims which follow.

German priority application 100 17 494.9 is relied on and incorporated herein by reference.

We claim:
1. A process for preparing trimethylhydroquinone diesters of the general formula (2)

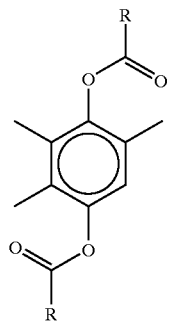

(2)

wherein R represents an optionally substituted aliphatic, alicyclic or aromatic hydrocarbon group,
and for producing 2,3,5-trimethylhydroquinone of the general formula (3)

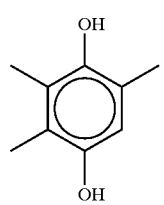

(3)

the process comprising reacting 2,2,6-trimethyl-cyclohexane-1,4-dione of the general formula (1)

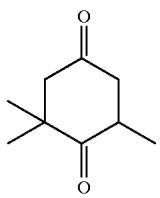

(1)

with an acylating agent, under oxidative conditions, with a sulfonating agent, and in the presence of a proton acid and/or a Lewis acid, at a temperature from −50° C. to 200° C., wherein the ratio between acylating agent and 2,2,6-trimethyl-cyclohexane-1,4-dione is at least 1.

2. The process according to claim 1, wherein the sulfonating agent comprises at least one member selected from the group consisting of sulfuric acid and oleum.

3. The process according to claim 1, wherein the acylating agent is selected from the group consisting of carboxylic anhydrides of the general formula (4)

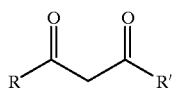

(4)

wherein R and R' are identical or different substituents, and represent an optionally substituted aliphatic, alicyclic or aromatic group having 1–10 carbon atoms, which may optionally be halogenated.

4. The process according to claim 1, wherein the acylating agent comprises acetanhydride.

5. The process according to claim 1, wherein the acylating agent comprises at least one member selected from the group consisting of carboxylic acid halides, enolesters, and ketenes.

6. The process according to claim 1, wherein the reaction is performed in the presence of at least one proton acid having a $pK_a$ value of 3 or less.

7. The process according to claim 1, wherein the reaction is carried out in the presence of at least one proton acid selected from the group consisting of nitric acid, perchloric acid, nitrous acid, hydrochloric acid, hydrobromic acid, hydrofluoric acid, methanesulfonic acid, ethanesulfonic acid, halosulfonic acids, perhaloalkanesulfonic acids, benzenesulfonic acid, para-toluenesulfonic acid, phosphoric acid, phenylphosphonic acid, nitroterephthalic acid, picric acid, trifluoroacetic acid, chloroacetic acid, mixtures of boric acid derivatives and chelating carboxylic acids, mixtures of boric acid and oxalic acid, oleum, sulfuric acid, and $HB(HSO_4)_4$—$H_2O_4$.

8. The process according to claim 1, wherein the reaction is carried out in the presence of at least one proton acid having a Hammett constant less than −11.9 (a superacidic acid).

9. The process according to claim 1, wherein the reaction is carried out in the presence of at least one solid acidic or solid superacidic catalyst used as the Lewis acid.

10. The process according to claim 9, wherein the acidic catalyst is provided in an amount of from 0.01 to 1000 mol. %, with respect to the 2,2,6-trimethylcyclohexane-1,4-dione.

11. The process according to claim 1, wherein the reaction is carried out in the presence of mixtures of Lewis acids and Brönsted acids.

12. The process according to claim 1, wherein the trimethylhydroquinone diacetate produced is saponified without first being isolated, optionally after distilling off unreacted acetanhydride, the saponification being carried out by adding water and/or dilute acid, and wherein the trimethyl hydroquinone produced is separated from the reaction mixture.

13. The process according to claim 1, wherein the trimethylhydroquinone diacetate produced is isolated from the reaction mixture, and is optionally saponified using dilute acid in the presence of a phase promoter, and wherein the trimethylhydroquinone produced is separated from the reaction mixture.

14. The process according to claim 13, wherein the phase promoter is at least one member selected from the group consisting of acetic acid, n-butanol and n-butyl acetate.

* * * * *

UNITED STATES PATENT AND TRADEMARK OFFICE
CERTIFICATE OF CORRECTION

PATENT NO. : 6,350,897 B2
DATED : February 26, 2002
INVENTOR(S) : Steffen Krill and Klaus Huthmacher It is certified that error appears in the above-identified patent and that said Letters Patent is hereby corrected as shown below:

Column 6,
Lines 1-7, change

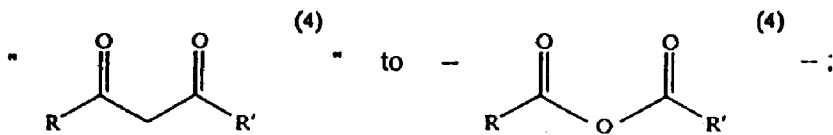

Column 11,
Lines 22-28, change

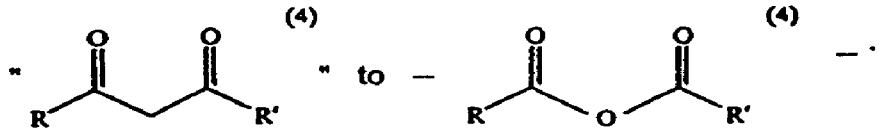

Signed and Sealed this

Third Day of September, 2002

Attest:

Attesting Officer

JAMES E. ROGAN
*Director of the United States Patent and Trademark Office*